US012539171B2

(12) United States Patent
Ruvio et al.

(10) Patent No.: US 12,539,171 B2
(45) Date of Patent: Feb. 3, 2026

(54) MICROWAVE ABLATION PROBE

(71) Applicant: Endowave Ltd., Dublin (IE)

(72) Inventors: Giuseppe Ruvio, Dublin (IE); Jimmy Eaton-Evans, Dublin (IE); Simon Hogan, Dublin (IE); Damian Carr, Dublin (IE)

(73) Assignee: ENDOWAVE LTD., Dublin (IE)

( * ) Notice: Subject to any disclaimer, the term of this patent is extended or adjusted under 35 U.S.C. 154(b) by 282 days.

(21) Appl. No.: 18/558,985

(22) PCT Filed: May 4, 2022

(86) PCT No.: PCT/EP2022/061986
§ 371 (c)(1),
(2) Date: Nov. 3, 2023

(87) PCT Pub. No.: WO2022/233938
PCT Pub. Date: Nov. 10, 2022

(65) Prior Publication Data

US 2024/0216060 A1 Jul. 4, 2024

(30) Foreign Application Priority Data

May 4, 2021 (EP) .................................... 21172155

(51) Int. Cl.
*A61B 18/18* (2006.01)
*A61B 18/00* (2006.01)

(52) U.S. Cl.
CPC ............................... *A61B 18/1815* (2013.01); *A61B 2018/00023* (2013.01); *A61B 2018/00577* (2013.01);
(Continued)

(58) Field of Classification Search
CPC ........ A61B 18/1815; A61B 2018/1884; A61B 2018/1892; H01B 13/016; H01B 13/0165; H05B 6/72; H01Q 13/0266; H01P 1/262
See application file for complete search history.

(56) References Cited

U.S. PATENT DOCUMENTS

2009/0187180 A1 7/2009 Brannan
2010/0217252 A1 8/2010 Rossetto et al.
(Continued)

*Primary Examiner* — Ronald Hupczey, Jr.
(74) *Attorney, Agent, or Firm* — Grogan, Tuccillo & Vanderleeden LLP

(57) ABSTRACT

A microwave ablation probe (100). The microwave ablation probe (100) comprises: an applicator (102) arranged to apply microwave radiation to heat surrounding tissue: a feed cable (104) arranged to supply electromagnetic energy to the applicator (102): a tubular shaft (105) arranged to house at least part of the length of the feed cable (104): a coolant flow path (106, 108) via which coolant is able to flow, the coolant flow path being located within a space between the tubular shaft (105) and the feed cable (102); and a choke (112) arranged to reduce power reflected from the applicator (102) along the feed cable (104). The choke comprises one or more bridging structures (114*a*. 114*b*. 14*c*) each provided on a component of the tubular shaft of the feed cable, the one or more bridging structures being arranged to extend across the space between the tubular shaft (105) and the feed cable (104) and form an electrical connection therebetween. The one or more bridging structures (114*a*. 114*b*. 114*c*) each extend only part way around a longitudinal axis of the ablation probe, thereby allowing coolant to flow through the choke (112). The one or more bridging structures (114*a*. 114*b*. 114*c*) are each formed from an angled region cut out from a wall of the component of the tubular shaft or the feeding cable from which they are formed.

17 Claims, 7 Drawing Sheets

(52) U.S. Cl.
CPC ................ *A61B 2018/1861* (2013.01); *A61B 2018/1892* (2013.01)

(56) References Cited

U.S. PATENT DOCUMENTS

| | | | | |
|---|---|---|---|---|
| 2011/0077635 | A1 | 3/2011 | Bonn | |
| 2015/0216596 | A1 | 8/2015 | Brannan | |
| 2016/0058508 | A1 | 3/2016 | Brannan | |
| 2016/0192987 | A1 | 7/2016 | Brannan et al. | |
| 2020/0188021 | A1* | 6/2020 | Wong | A61B 34/30 |
| 2020/0205894 | A1 | 7/2020 | Eaton-Evans et al. | |

* cited by examiner

MICROWAVE ABLATION PROBE

CROSS-REFERENCE TO RELATED APPLICATIONS

This application is a national stage of International Application No. PCT/EP2022/061986 filed on May 4, 2022, which claims priority to EP Patent Application No. 21172155.0 filed May 4, 2021, all of which is hereby incorporated by reference in its entirety.

FIELD OF THE INVENTION

This application relates to a microwave ablation probe. In particular, this application relates to an ablation probe that may be used to generate heat within tissue to destroy tissue.

BACKGROUND OF THE INVENTION

Thermal ablation can be used to destroy tissue growths within the body which can be malignant. Current ablation systems use applicators that deliver Radio Frequency (RF) energy or microwave energy to the tissue surrounding an applicator tip. This causes localised heating and destruction of the malignant cells.

SUMMARY OF THE INVENTION

Known ablation probes comprise an active tip (or applicator) generally made of ceramic material which is coupled to a coaxial feed cable arranged to supply electromagnetic energy to the active tip. Where the feed cable is connected to the active tip a back current may be reflected back along the feed cable. This is particularly the case for microwave ablation. These currents can subtract power from the ablation zone around the applicator in the targeted tissue region and generate a tear-shaped ablation zone. A spherical ablation zone is however advantageous during use of the ablation probe in order to provide better control of the treatment being carried out.

A choke (also known as a balun) is a microwave component that is known to mitigate back currents running on the outer conductor of a feed cable supplying electromagnetic energy to an applicator or antenna. An example of a prior art choke is shown schematically in FIG. 1. In this example, a feed cable 2 is coupled to an active tip 4. The feed cable comprises an inner conductor 6 and an outer conductor 8. The inner conductor 6 can be seen extending into the active tip 4. In this example, the choke is formed by a metallic pocket 10 located at the base of the active tip 4. The metallic pocket is formed from a conducting sleeve that is spaced apart from and extends around the feed cable. The sleeve is electrically connected to the outer conductor of the feed cable 2 by the base of the choke (also known as a balun short). The choke generates image currents (labelled 'A') opposite in phase to the reflected current (labelled 'B') that help mitigate back currents on the outer conductor 108 of the feed cable.

The applicant is aware of US2015/216596 A1, US2016/192987 A1 and US2009/187180 which disclose choke structures similar to that shown in FIG. 1. In these examples, an insulator or dielectric material is included between the feeding cable and balun sleeve. In order to cool the choke water is allowed to flow around the outer surface of the balun sleeve by placing it in within a coolant flow conduit of the ablation probe.

Choke designs such as this have a number of draw backs. Chokes with solid (either ceramic or plastic) dielectric materials are cooled only externally. This reduces the cooling efficiency. The use of solid materials also has an impact on miniaturisation, and reduces the flexibility of the ablation probe which can be important where they are to be used endoscopically or with other similar delivery devices.

The applicant is also aware of US2016/0058508 A1, which discloses an ablation probe comprising a tubular sheath and a coaxial feedline, including an outer conductor. A balun short is disposed in electrical communication around the outer conductor, the balun short including at least one longitudinal notch. A conductive tube is disposed coaxially around the balun short and within the tubular sheath, the conductive tube defining at least one fluid conduit. An inflow tube is disposed longitudinally along the outer conductor and at least partially within the at least one notch. The balun short further includes an outflow notch through which coolant may exit from a coolant chamber supplied by the inflow tube. Drawbacks of designs such as this include limited coolant flow through the balun short. This impedes coolant flow around the device that is needed to ensure cooling of the applicator during use. The balun short is also difficult to miniaturise while still being suitable for manufacture and assembly.

The present application aims to address at least some of these problems. A general problem to be solved is how to provide a choke to control the shape an ablation zone that is adequately cooled, small in size and suitable for manufacture and assembly.

An aspect of the present disclosure provides a microwave ablation probe, comprising any one or more of:

a. an applicator arranged to apply microwave radiation to heat surrounding tissue;

b. a feed cable arranged to supply electromagnetic energy to the applicator;

- a tubular shaft arranged to house at least part of the length of the feed cable;
- a coolant flow path via which coolant is able to flow, the coolant flow path being located within a space between the tubular shaft and the feed cable; and
- a choke arranged to reduce power reflected from the applicator along the feed cable, wherein:
- the choke comprises one or more bridging structures each provided on a component of the tubular shaft or the feed cable, the one or more bridging structures being arranged to extend across the space between the tubular shaft and the feed cable and form an electrical connection therebetween,
- the one or more bridging structures each extend only part way around a longitudinal axis of the ablation probe, thereby allowing coolant to flow through the choke, and
- the one or more bridging structures are each formed from an angled region cut out from a wall of the component of the tubular shaft or the feed cable from which they are formed.

The bridging structures of the first aspect are advantageous in forming a choke that allows coolant flow through its base to ensure efficient cooling of the device, along with providing a structure that appears closed to microwaves to ensure suitable choke operation. Moreover, by forming the bridging structures so that they are cut out from part of the tubular shaft or part of the feed cable they are more easily and accurately manufactured and assembled, particularly when using small components.

Each of the bridging structures may be formed from a tab or strip of material that is cut out from the wall of the respective component from which it is formed. The material forming each bridging structure is deformed or bent so that it is an angled part of the wall of the component from which it is formed.

Each of the bridging structures therefore comprises an angled (i.e. bent or otherwise deformed) region of the wall of a component of the tubular shaft or feed cable from which it is formed, the angled region being defined (i.e. formed or created) by at least one cut-out in the wall of the component.

Each of the bridging structures may therefore be a bent tab or strip. The bridging structures may form a bridging strut between the tubular shaft and feed cable.

The bridging structures may form a resiliently deformable structure. This may aid a close fit being formed between the bridging structures and the component of the tubular shaft or feed cable which they contact to make an electrical connection.

The one or more bridging structures are formed in an element or component of the tubular shaft and/or the feeding cable. They may be formed in any one or more of a feed cable sleeve forming part of the feed cable, a shaft sleeve forming part of the tubular shaft, or a tubular member forming part of the tubular shaft.

The feed cable may comprise a feed cable sleeve forming an outer part of the feed cable and which is electrically connected to an electrical conductor of the feed cable. The tubular shaft may comprise a tubular member extending along the length of the ablation probe and surrounding the feed cable. An outside surface of the feed cable sleeve may be spaced apart from an inside surface of the tubular shaft (e.g. the tubular member) to form the space in which the coolant flow path is located. The one or more bridging structures may each be formed from a region (e.g. the wall) of the feed cable sleeve.

The feed cable sleeve may be close fitting around the outer conductor (or other outer surface) of the feed cable. The feed cable sleeve may be electrically connected to the outer conductor of the feed cable and is itself electrically conducting.

The tubular shaft may comprise a tubular member and a shaft sleeve located within the tubular member. An outside surface of the feed cable may be spaced apart from an inside surface of the shaft sleeve to form the space in which the coolant flow path is located. The one or more bridging structures may each be formed from a region (e.g. the wall) of the shaft sleeve.

The shaft sleeve may be electrically conducting to form part of the choke. The shaft sleeve may be in electrical connection with the feed cable via its bridging structures. The tubular shaft may form a close fit around the shaft sleeve.

The tubular shaft may comprise a tubular member. An outside surface of the feed cable may be spaced apart from an inside surface of the tubular member to form the space in which the coolant flow path is located. The one or more bridging structures may each be formed from a region (e.g. the wall) of the tubular member.

At least the region of the tubular member having the bridging structures may be electrically conductive to form part of the choke, and may be electrically connected to the feed cable via its bridging structures.

The tubular shaft may further comprise a sealing sleeve extending around the outer surface of the tubular member at the location of the bridging structures. The sealing sleeve may be arranged to seal cut-outs in the wall of the tubular member formed by each of the one or more bridging structures when they are formed in the tubular member. This may seal the coolant flow path within the tubular member.

The angled region of each bridging structure may extend out of alignment with an inner or outer surface of the component of the feed cable or tubular shaft from which it is formed. The bridging structures thus form a region splayed outward or inward from the surface of the component from which it is formed.

One or each of the one or more bridging structures may comprise a bent strip extending between a distal section and a proximal section of the respective component of the tubular shaft or feed cable from which they are formed.

Each of the bent strips may have a rounded region at the point of contact with the other of the component of the tubular shaft or a component of the feeding cable. The rounded region may form the point of contact between the bridging structures and the component of the tubular shaft or feed cable to which they make an electrical contact (i.e. the component of the tubular shaft or feed cable which they contact rather than being formed from).

One or each of the one or more bridging structures may comprise a bent tab connected at one end to the body of the component of the feed cable or tubular shaft from which it is formed.

Each of the one or more bridging structures may extend an angle around the longitudinal axis of the ablation probe in the range between 5° and 100°.

The bridging structures may be arranged to concentrically align the feed cable and the tubular shaft. This may help to keep the feed cable and tubular shaft separated so that electrical contact and points other than the bridging structures does not occur. This would otherwise reduce the performance of the choke.

The one or more bridging structures may be a plurality of bridging structures angularly spaced apart around a longitudinal axis of the ablation probe. Spacing apart of the bridging structures allows space for coolant to flow between them.

The one or more bridging structures may comprise at least three (or three) spaced apart bridging structures. At least three bridging structures may be advantageous to help ensure concentricity.

The plurality of bridging structures may be spaced apart by an angle around the longitudinal axis of the ablation probe in the range between 20° and 115°.

The range of sizes of bridging structure and angle between them give in the statements above may allow for adequate space for coolant to flow between them without requiring excessive pressure, while still providing a base for the choke that can prevent microwaves being reflected back along the feed cable. The angles may apply to embodiments where there are three bridging structures, but may also apply to other embodiments in which other numbers are provided.

In some embodiments, the coolant flow paths may extend an angle in the range between 60° and 80° (e.g. corresponding to the angular spacing between the bridging structures). In some embodiments, the bridging structures may extend an angle in a range between about 40° and 60°.

The coolant flow path may be a first coolant flow path, and the microwave ablation probe may further comprise a second coolant flow path. The first coolant flow path may be formed by a coolant conduit disposed within the tubular shaft (e.g. within the tubular member of the tubular shaft, and within the shaft sleeve if present). The coolant conduit may extend along the longitudinal axis of the feed cable between two of the plurality of bridging structures. The second coolant flow path may be provided by the space or spaces between the other remaining bridging structures. This may provide a compact arrangement of coolant flow channels with the tubular shaft.

Alternatively, only one of the first and second coolant flow paths may be provided within the tubular member of the tubular shaft. The tubular shaft may comprise a first inner tubular member and a second outer tubular member. The first and second tubular members may be spaced apart from each other to form a coolant flow path therebetween (e.g. to form one of the first and second coolant flow paths, the other being within the first tubular member). This provides a concentric arrangement of coolant flow paths.

The coolant conduit may be shaped to conform to the shape of an inner surface of the tubular shaft and an outer surface of the feed cable between which it extends. This may help to maximise the space available for coolant to be carried.

The coolant conduit may have a flattened (e.g. non-circular) cross sectional profile in a plane normal to the longitudinal axis of the ablation probe. This may help to provide a compact arrangement while maximising the space for coolant flow. The coolant conduit may be sized/shaped to fit within the annular sector between bridging structures.

Any features described above in connection with one aspect or statement may be used, unless where mutually exclusive, in combination with any other aspect or statement.

As used herein, a range "from value X to value Y" or "between value X and value Y", or the like, denotes an inclusive range; including the bounding values of X and Y. Angles are given in degrees unless otherwise stated.

BRIEF DESCRIPTION OF THE DRAWINGS

Embodiments of the invention will now be described, by way of example only, with reference to the accompanying drawings, in which.

DETAILED DESCRIPTION

Figure 2:
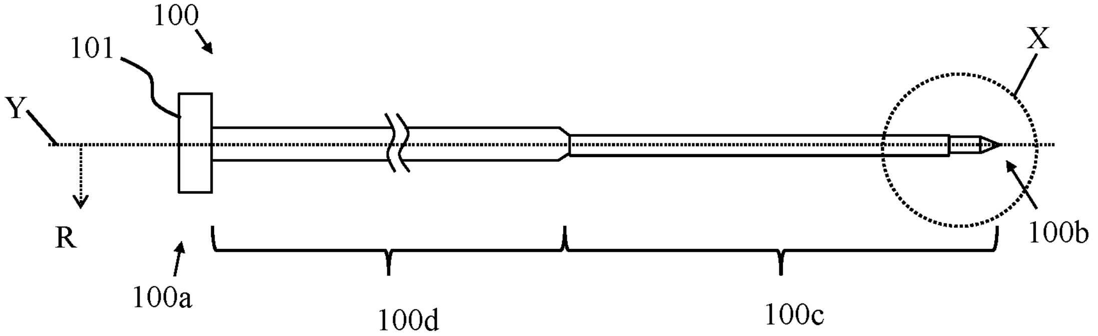
FIG. 2 shows a side view of an ablation probe according to an embodiment.

An ablation probe 100 according to an embodiment is shown schematically in FIG. 2. Further views of the ablation probe and its various components are shown in FIGS. 3 to 11. The ablation probe 100 of the present disclosure may be suitable for insertion into the body to reach a desired treatment site, such as a malignant tissue growth. In order to reach a desired treatment site, the ablation probe may be suitable for insertion through the working channel of an internal anatomy access device. By internal anatomy access device we mean any device which may be placed within the anatomy of a patient, the device having a working channel for insertion of instruments to a desired location within the body. The internal anatomy device may be an intraluminal delivery device arranged to be delivered along an anatomical lumen of the patient (e.g. the trachea and the pathways of the bronchi in the lungs or the oesophagus). The ablation probe 100 may, for example, be used endoscopically or using an ENB system in order to reach a variety of disease locations within the body. The ablation probe may therefore have an overall flexibility such that it can be inserted through the working channel of the endoscope. In other embodiments, the ablation probe may be used with other types of intraluminal delivery device such as specific types of endoscope (e.g. a bronchoscope) or a navigation system such as a lung navigation system (e.g. an ENB system). In other examples, the ablation probe 100 may also be used percutaneously, or using any other suitable technique, e.g. inserted through an existing aperture of the body. For percutaneous use, the ablation probe may be generally rigid so that it can be inserted.

The ablation probe extends between a proximal end 100*a* and a distal end 100*b*. The terms "distal" and "proximal" are taken relative to the user operating the ablation probe and the treatment site when the ablation probe is positioned for use—the distal end 100*b* of the ablation probe 100 is that closest to the treatment site and the proximal end 100*a* is that closest to the user. The ablation probe 100 has a longitudinal axis Y that extends the length of the device between the distal and proximal ends. A radial direction R is defined as a direction normal to the longitudinal axis Y as shown in FIG. 2.

A handle 101 is provided at the proximal end of the ablation probe 100 so that it can be manipulated and positioned by the user. The distal end 100*b* may be fed through the working channel of an endoscope or similar device to reach a target ablation site.

Figure 3:
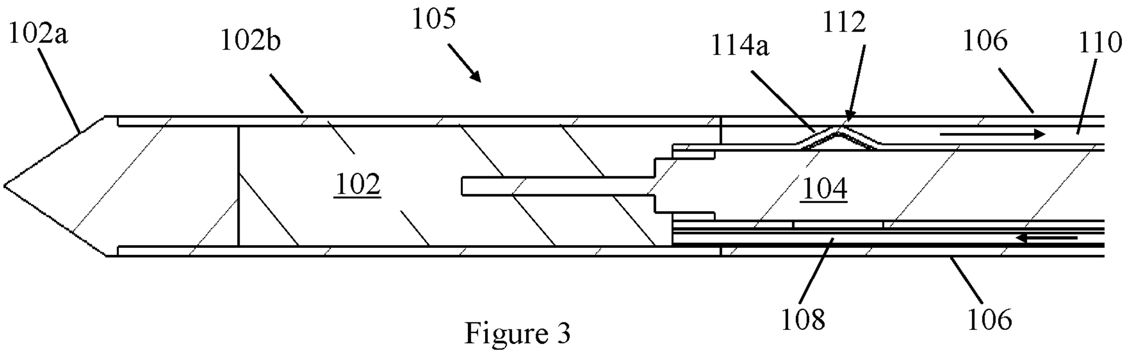
FIG. 3 shows a close up cross sectional view (along a longitudinal axis) of the distal region of the ablation probe of FIG. 1.

A cross sectional view of the distal region X of the ablation probe 100 is shown in FIG. 3. The ablation probe 100 generally comprises an applicator 102, a feeding or feed cable 104 and a tubular shaft 105 in which the feeding cable 104 is located. The terms "feeding cable" and "feed cable" are used interchangeably herein.

The applicator 102 is arranged to apply radiation to heat surrounding tissue. The applied radiation may be adapted to cause localised heating and destruction of malignant cells around or near to the applicator 102. The applicator 102 may be arranged to apply any suitable form of radiation to surrounding tissue such that the desired heating is caused. The applicator 102 may, for example, be arranged to emit microwave or RF radiation, or may emit any other suitable radiation to cause heating. The applicator 102 is arranged at or near a distal end of the ablation probe 100 so that it can be positioned in a desired position relative to the tissue to be treated. The applicator 102 may be formed from a ceramic material with suitable dielectric properties (for example, zirconia) according to the energy it is arranged to apply.

The feed or feeding cable 104 is arranged to supply electromagnetic energy to the applicator 102. Only part of the length of the feeding cable is shown in the Figures. The feeding cable 104 may be any elongate member suitable for supplying electromagnetic energy to the applicator (e.g. a conductor). The feeding cable 104 may run along at least part or all of the length of the ablation probe 100 to deliver a supply of energy to the applicator 102. In the described embodiment, a distal end of the feeding cable 104 is coupled to a proximal end of the applicator 102 and a proximal end of the feeding cable 104 (not shown in the Figures) is coupled to a generator (also not shown in the Figures) suitable for generating the desired signal to supply energy to the applicator 102. In the presently described embodiment, the feeding cable 104 comprises a coaxial cable. The coaxial cable comprises an inner conductor 104*a* insulator 104*b*, and outer conductor 104*c*. The feed cable 104 may comprise further components such as an outer sleeve as described later.

In the present embodiment, an applicator tip 102*a* is connected to the distal end of the applicator. The tip 104*a* forms a pointed distal tip of the ablation probe 100 that is suitable for piercing tissue in use. In other embodiments, the separate tip component may not be provided, or may be formed integrally with the applicator 102. In yet other embodiments, the ablation probe may have an atraumatic distal tip, rather than a pointed one. The tip 102*a* is coupled to the applicator 102 via a capsule 102*b*, which is arranged to house the applicator 102. The capsule 102*b* may be a tubular component surrounding the ceramic material of the applicator as shown in the Figures. The applicator 102, applicator tip 102*a* and capsule 102*b* form an applicator assembly.

Referring again to FIG. 3, the tubular shaft 105 comprises a tubular member 106 (such as a sheath or other such hollow elongate component (e.g. a hypotube, or braid/coil reinforced tubing)) arranged to house at least part of the length of the feeding cable 104. The tubular member 106 may be formed from a metal material which has sufficient rigidity to allow the ablation probe to be inserted into tissue. In other embodiments, the tubular member 106 may be formed from any other suitable material, and may be formed from a superelastic material, for example Nitinol.

Figure 1:
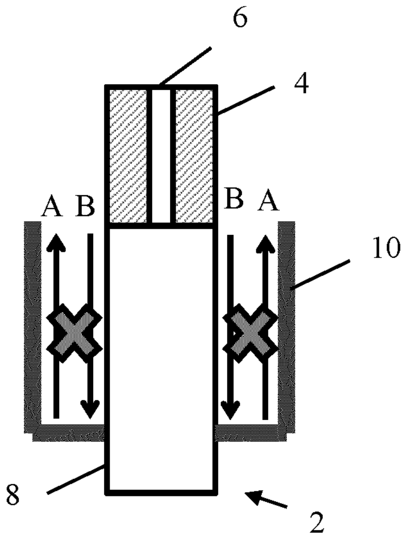
FIG. 1 shows an example of a prior art choke.

Referring again to FIG. 1, the ablation probe 100 generally comprises two portions: a needle portion 100*c* and a catheter portion 100*d*. The needle portion 100*c* may be arranged at the distal end of the ablation probe 100 and is adapted to be inserted into tissue during use to reach the desired ablation location. The catheter portion 100*d* may be provided at the proximal end of the ablation probe 100 and is arranged to supply electromagnetic energy and a flow of coolant to and from the needle portion 100*c*. The catheter portion 100*d* may have an extended length and flexibility for endoscopic use. In other embodiments, a shorter, more rigid catheter portion 134 may be provided for percutaneous use.

In some embodiments, the needle portion 100*c* may form a small part of the overall length of the ablation probe. For example, the needle portion may be 5 mm to 2000 mm in length, and preferably may be around 70 mm in length. The length of the needle portion 100*c* may be chosen according to the anatomy to be accessed. For example, the needle portion may be approximately between 10 and 100 mm long for delivery of therapy to organs including the pancreas, or lung, or longer (for example 100-400 mm in length) for delivery of therapy percutaneously. A longer length of needle portion may be more suitable for accessing parts of the lung, for example. The catheter portion may be around 1000 mm to 2000 mm in length, and preferably around 1400 mm in length. The length of the catheter portion may be chosen according to the position of the ablation site which must be reached.

In other embodiments, the needle portion 100*c* of the ablation probe may form a greater proportion of the length of the ablation probe. In some embodiments, the entire length of the ablation probe may be formed by the needle portion 100*c* (i.e. such that a separately defined catheter portion is absent). For example, if the ablation probe is to be used percutaneously the catheter portion 100*d* may be shorter than for endoscopic use, or may not be required.

The ablation probe 100 further comprises a coolant circuit flow path forming a coolant supply circuit. The flow of coolant is shown by arrows in FIGS. 3 and 6. The coolant circuit comprises a first coolant path 108. In the described embodiment, the first coolant path 108 is a coolant delivery path via which coolant is able to flow in a direction towards the applicator 102. For example, the coolant delivery path 108 may deliver a flow of coolant towards the distal end of the ablation probe 100 from a coolant supply (not shown in the Figures) coupled to the coolant delivery path 108 at the proximal end of the ablation probe 100. The coolant may be pumped around the coolant circuit by a suitable pump such as a peristaltic pump. The flow of coolant may help control the temperature of the ablation probe 100 during use. This may allow energy to be delivered to the surrounding tissue for an extended period of time without the ablation probe 100 overheating and being damaged, or causing injury to healthy tissue. The coolant may be a fluid, and may be water, saline solution, a cryogenic gas or any other suitable coolant known in the art.

The coolant circuit flow path further comprises a second coolant path 110. In the described embodiment, the second coolant path 110 is a coolant return path via which coolant can return from the applicator 102. The coolant return path 110 may therefore return the supply of coolant from the distal end of the ablation probe 100 to the proximal end.

The first and second coolant flow paths are fluidly connected in the distal region of the ablation probe so as to form the coolant circuit. The first and second coolant flow paths may be connected by any suitable arrangement of channels or conduits, e.g. within the applicator assembly so that the applicator is cooled. For example, the coolant flow paths may be linked by channels or conduits formed within the ceramic material of the applicator 102 so that a continuous coolant circuit is formed.

In the presently described embodiment, both of the first and second coolant flow paths are located within the tubular member 106. The inner surface of the tubular member 106 is spaced apart from the outer surface of the feeding cable 104 as will be described in more detail later on. The first coolant flow path is defined by a coolant conduit 108*a* located within the tubular member. The coolant conduit 108*a* extends along the length of the feeding cable 104 to carry coolant to the distal region. The second coolant flow path is defined by an inner surface of the tubular member 106 and outer surface of the feed cable 104.

In other embodiments, the first coolant path 108 may act as a coolant return path. In this embodiment, the first coolant path 108 is arranged to carry a flow of coolant away from the applicator. In this embodiment, the second coolant path 110 may act as a coolant delivery path arranged to carry a flow of coolant towards the applicator. A combination of the first and second coolant paths may therefore form a coolant circuit arranged to deliver a flow of coolant towards and away from the applicator, where the coolant can flow in either direction along each of the first and second coolant paths.

The ablation probe 100 further comprises a choke 112 arranged to reduce power reflected from the applicator along the feed cable. In the present embodiment, the choke 112 is partly formed by an electrically conducting distal region of the tubular member 106 that surrounds the feeding cable 104. In order to provide an electrical connection between the feeding cable 104 and the tubular member 106 the choke comprises three bridging structures (or bridging members or struts) 114*a*, 114*b*, 114*c*. The bridging structures are arranged to extend across the space between the tubular member 106 and feeding cable 104 to provide an electrical connection between them. The bridging structures therefore form the base of the choke (i.e. the choke short). The bridging structures have spaces between them though which one or both of the first and second coolant flow paths may be located. This allows coolant to flow through the base of the choke, rather than around it, to improve cooling and help to make the ablation probe more compact. By forming the bridging structures from cut out regions of material they can be made in flexible components suitable for ensuring the ablation probe has an overall degree of flexibility for endoscopic (or similar) use.

In the presently described embodiment three (axially aligned) bridging structures are provided. Three bridging structures may be used to ensure concentricity between the feed cable 104 and the tubular member 106 (preventing undesired points of electrical contact effecting the operation of the choke). By using three bridging structures they may be sized to ensure concentricity, while still being suitable for manufacture. In other embodiments, other numbers of axially aligned bridging structures may be provided, so that more generally the ablation probe comprises at least one bridging structure. For example, it may also be possible to achieve concentricity with fewer bridging structures (e.g. one or two) that span a greater circumferential length around the feeding cable (e.g. angle α shown in FIG. 10). In other embodiments, more than three axially aligned bridging structures may also be provided, which may also provide a suitable concentric arrangement. In this paragraph axially aligned means at the same location along the length (longitudinal axis Y) of the ablation probe e.g. the same distance along the feed cable from the point of connection with the applicator. In some embodiments there may be further sets of non-axially aligned bridging structures as will be described later.

In the described embodiment, the portion of tubular member 106 surrounding the feeding cable 104 that extends distally from the bridging structures is formed from an electrically conductive material so that it forms part of the choke. In some embodiments, a larger region or all of the tubular member 106 may be formed from an electrically conductive material.

The three bridging structures 114*a*, 114*b*, 114*c* are located at the same distance from the proximal end of the applicator 102 along the longitudinal axis Y of the ablation probe (i.e. the point of electrical contact between the bridging structures 114*a*, 114*b*, 114*c* is the same distance from the applicator). They therefore form a first set of one or more axially aligned bridging structures. The distance between the point of electrical contact between the bridging structures 114*a*, 114*b*, 114*c* and tubular member 106 is proportional to approximately a multiple of an odd number of one quarter of the wavelength of the electromagnetic energy corresponding to the operating frequency of the ablation probe, or the wavelength of the electromagnetic energy in a medium surrounding the feeding cable 104 (e.g. the media within the choke). One or more further sets of bridging structures may be provided, each set being spaced apart along the length of the ablation probe by a similar multiple of an odd number of one quarter of the wavelength. This separation distance allows image currents in the choke to be provided which have the opposite phase to reflected current running back along the feeding cable.

As can been seen in the Figures, the feeding cable comprises a feed cable sleeve 116 that fits around the outer surface of the outer conductor. The feed cable sleeve 116 therefore forms an outer part or surface of the feed cable that is spaced apart from an inner surface of the tubular shaft (e.g. the tubular member in the present embodiment) in which it is housed. The bridging structures 114*a*, 114*b*, 114*c* are each formed from part of the sleeve 116. In the present embodiment, the sleeve 116 forms a close fit around the outer conductor of the feeding cable 104. In other embodiments, the sleeve may extend around an insulating layer around the outer conductor of the feeding cable. The sleeve is formed from an electrically conductive material, and is electrically connected to the outer conductor of the feed cable 104.

Each of the bridging structures 114*a*, 114*b*, 114*c* is formed from a respective deformed or angled region that is cut out from the wall of the sleeve 116. The deformed region extends out of alignment with the body of the sleeve 116 to extend across the gap between the feeding cable 102 and the tubular member 106. The bridging structures 114*a*, 114*b*, 114*c* therefore extend at least partly in the radial direction R relative to the longitudinal axis Y of the ablation probe. The bridging structures 114*a*, 114*b*, 114*c* are each formed from a strip of material cut-out from the body of the sleeve 116. The strips are bent or deformed so that they are out of alignment with the outer surface of the sleeve 116. The bridging structures are therefore splayed-out from the sleeve outer surface. In the present embodiment, the bridging structures 114*a*, 114*b*, 114*c* are therefore formed integrally with the body of the sleeve 116. By forming the bridging structures from a section of material defined by a cut-out or cut-outs in the body of the sleeve they may be more easily manufactured and assembled. In order to separate the strips or regions forming the bridging structures the sleeve may be laser cut. This provides accurate cutting. Other forms of cutting may however be used.

By forming the bridging structures 114*a*, 114*b*, 114*c* in this way they form a resiliently deformable structure. This allows them to be compressed (e.g. pushed back towards alignment with the outer surface of the sleeve 116) when inserted into the tubular member during assembly of the ablation probe. An interference fit is therefore provided between the bridging structures 114*a*, 114*b*, 114*c* and tubular member 106. This helps to ensure electrical contact is maintained between the bridging structures 114*a*, 114*b*, 114*c* and tubular member 106, without needing to manufacture components to a very narrow tolerance range.

Figure 11:
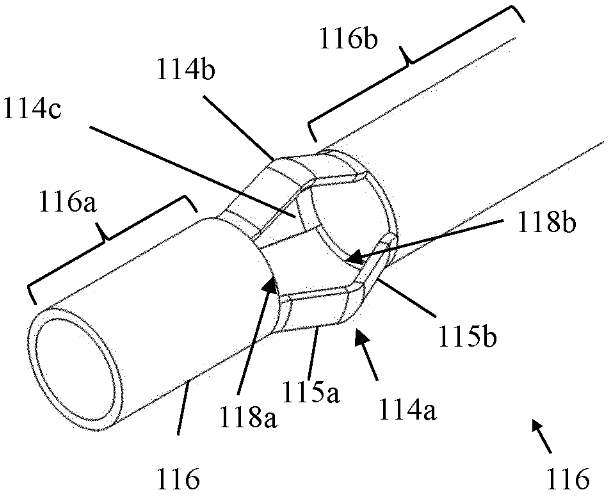
FIG. 11 shows a perspective view of the sleeve shown in FIG. 10.

In the presently described embodiment, the bridging structures 114*a*, 114*b*, 114*c* each form strips extending between a distal portion 116*a* and a proximal portion 116*b* of the sleeve 106. The bridging structures therefore comprise two oppositely angled sections 115*a*, 115*b* as can be seen in FIG. 11. The axially extending edges of the strips forming the bridging structures 114*a*, 114*b*, 114*c* are separated from the body of the sleeve member by three cuts-outs 118*a*, 118*b*, 118*c* (two of which are visible in the Figures).

In order to manufacture the bridging structure, the cut-outs forming the bridging structures are first formed in the sleeve to divide it into the distal and proximal sections 116*a*, 116*b*. Force is then applied at the distal and proximal ends of the sleeve in a direction along its axial length towards its centre. This compresses the length of the sleeve 116, and causes the strips forming the bridging structures to deform or splay out of alignment with the outer surface of the sleeve 116.

The bridging structures 114*a*, 114*b*, 114*c* each comprise a rounded portion at the point of contact with the tubular member 106.

Figure 4:
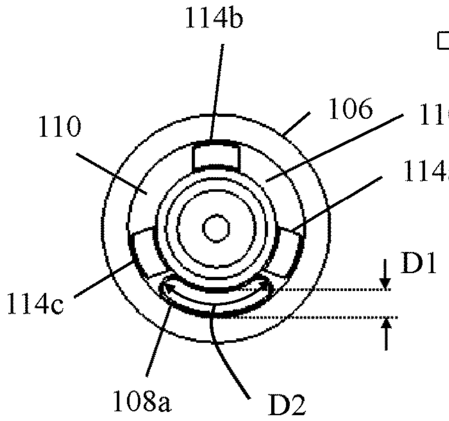
FIG. 4 shows a cross sectional view (in a plane normal to the longitudinal axis) of the ablation probe in FIG. 1 at the position of the base of a choke included in the ablation probe.
Figure 5:
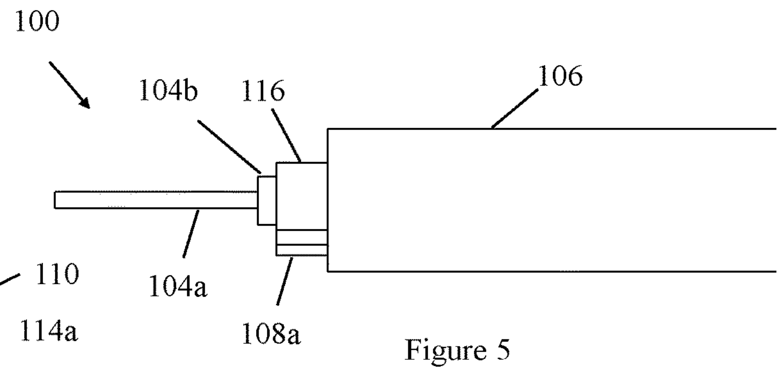
FIG. 5 shows a partly assembled side view of the ablation probe of FIG. 1, without its applicator assembly.
Figure 6:
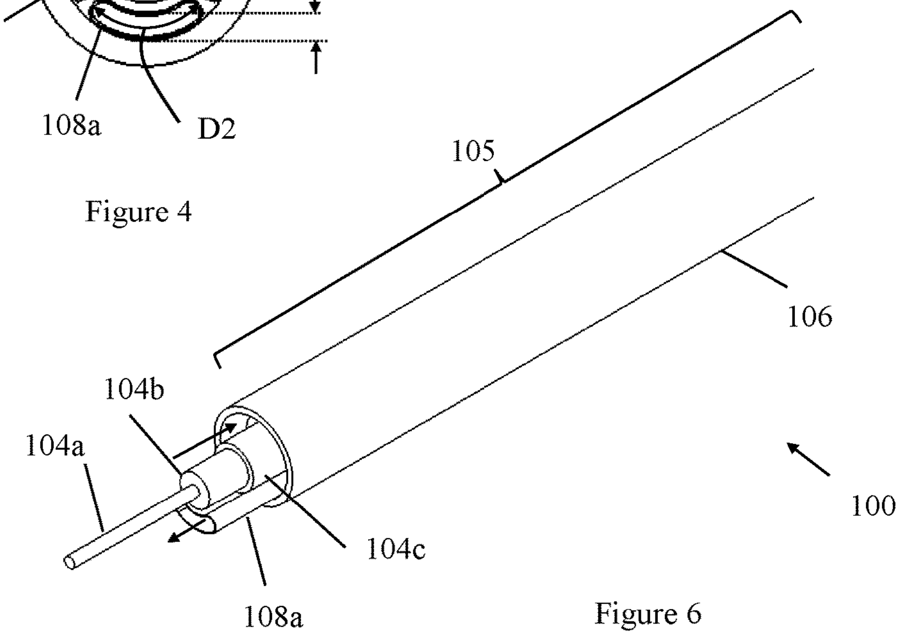
FIG. 6 shows a perspective view corresponding to FIG. 5.
Figure 7:
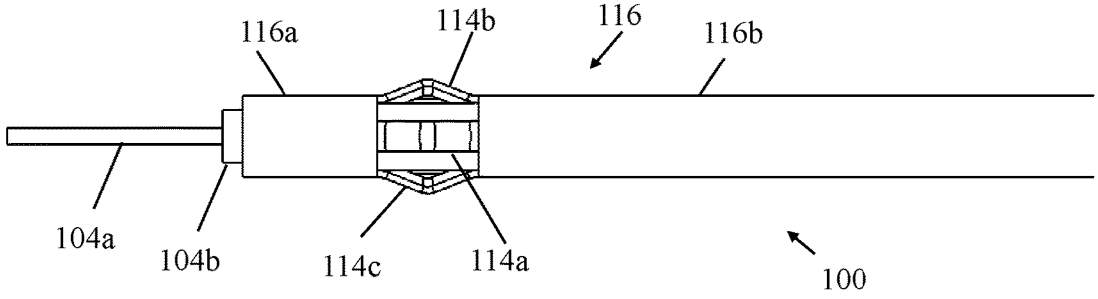
FIG. 7 shows a partly assembled side view of the ablation probe of FIG. 1, without the tubular member and applicator assembly.
Figure 8:
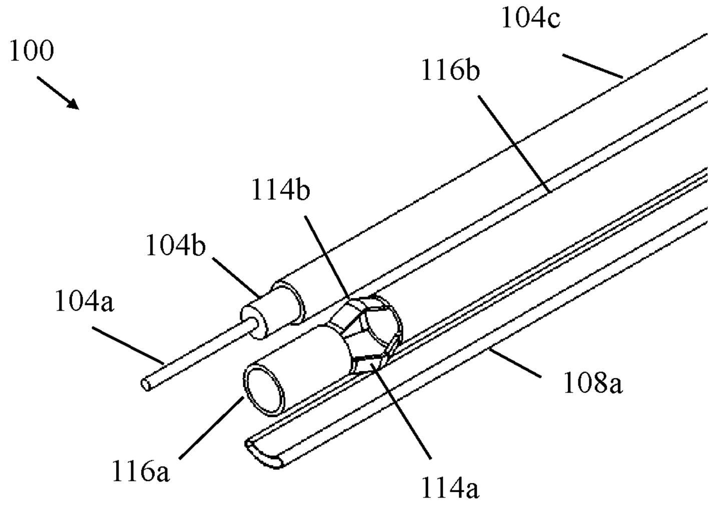
FIG. 8 shows an exploded perspective view of the components shown in FIG. 7.
Figure 9:
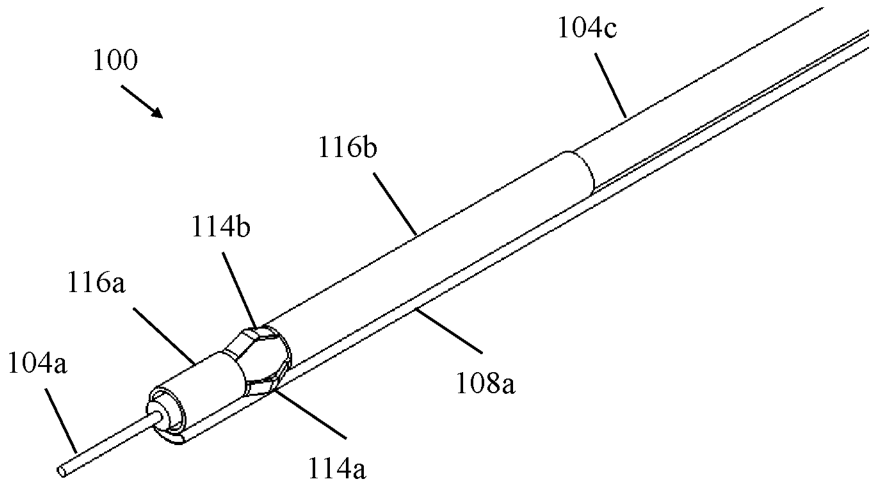
FIG. 9 shows an assembled perspective view of the components shown in FIG. 8.
Figure 10:
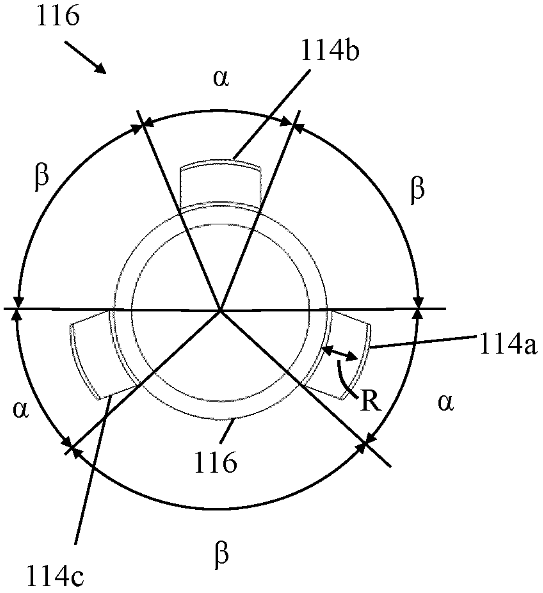
FIG. 10 shows a cross sectional view (in a plane normal to the longitudinal axis) of a sleeve forming part of the choke of the ablation probe of FIG. 1.

As can be seen in the cross section of FIGS. 4 and 10, the bridging structures 114*a*, 114*b*, 114*c* are angularly spaced apart around the longitudinal axis Y. A space is therefore formed between each of the bridging structures 114*a*, 114*b*, 114*c* which can be used to allow coolant to flow. In the presently described embodiment, the bridging structures are evenly spaced (they have an equal angle between them) around the longitudinal axis Y and extend an equal distance radially from the outer surface of the sleeve 116. By providing three or more evenly spaced bridging structures of equal radial extent from the sleeve 116 the tubular member 106 is held in a concentric alignment with the feeding cable 104. This ensures that the feeding cable 104 remains spaced apart from the surrounding tubular member 106 so that there is no electrical connection between them other than that provided by the bridging structures 114*a*, 114*b*, 114*c*. This would otherwise lead to a loss of choke performance. In other embodiments, as mentioned above, a greater number of bridging structures (e.g. more than three) may be provided, or fewer than three bridging structures can be used. In both cases a concentric alignment may still be provided. In some embodiments, some or all of the bridging structures may not be evenly angularly spaced around the longitudinal axis Y.

The space between the bridging structures is used to provide space for the first and second coolant flow channels. The coolant conduit 108*a* forming the first coolant flow path 108 is arranged to extend between two of the bridging structures 114*a*, 114*c* as can be seen in FIG. 4. The remaining two spaces between the bridging structures provides space for the second coolant flow path 110, which in the present embodiment is defined by the inner surface of the tubular member 106 and the outer surface of the sleeve 116.

Referring to FIG. 10, the coolant flow paths defined between the bridging structures (i.e. the angle at which they are spaced apart) extend an angle ß of about 70° around the longitudinal axis. In other embodiments, the coolant flow paths may extend an angle in the range between 60° and 80° (again corresponding to the angular spacing between the bridging structures). By providing coolant flow paths sized within this range the base of the choke has the desired electromagnetic properties to reduce microwaves reflected from the applicator, while still allowing sufficient space to accommodate coolant flow paths of sufficient size without needing excessive coolant pressure. In the present embodiment in which there are three bridging structures, each of the bridging structures 114*a*, 114*b*, 114*c* extend an angle $\alpha$ of about 50° around the longitudinal axis Y. In other embodiments, the bridging structures may extend an angle in a range between about 40° and 60°, according to the desired space between them for coolant to flow.

Figure 20:
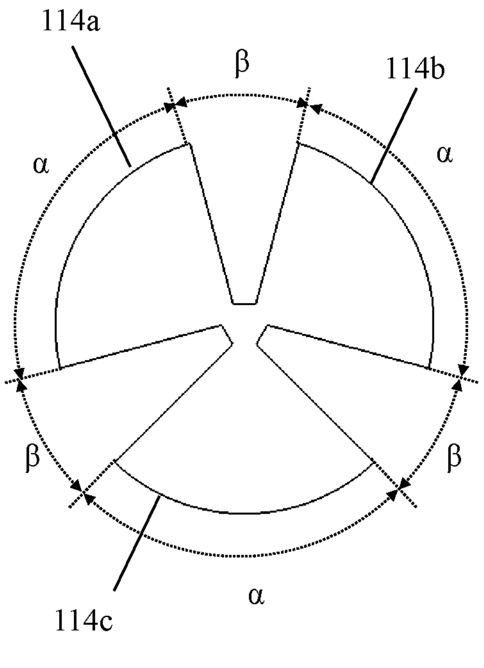
FIGS. 20 and 21 illustrate bridging structures having different angular sizes and spacing.
Figure 21:
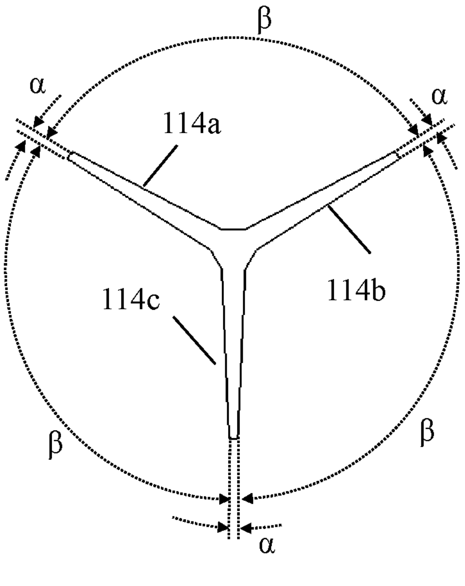

The angular sizes ($\alpha$) and spacing ($\beta$) in the previous paragraph may apply to other embodiments in which other numbers of bridging structures are provided. The number of bridging structures and their size can be adjusted to accommodate different angular spacing between them, or vice versa. More generally therefore, the angular spacing between bridging structures (B) may be in the range between 20° and 115°. Correspondingly, the angular size (a) of the bridging structures may be in the range between 5° and 100°. Examples of bridging structures with a small spacing and a relatively large spacing are shown in FIGS. 20 and 21. In the various embodiment described the bridging structures are equal in size and spacing as shown in the Figures to aid manufacture and concentric alignment. In other embodiments, they may have different sizes/spacing to each other.

The coolant conduit 108*a* has a flattened non-circular cross sectional profile (in a plane normal to the longitudinal axis Y). The coolant conduit 108*a* is shaped to conform to the shape of an inner surface of the tubular member 116 and an outer surface of the feed cable 104 between which it is located. The coolant conduit 108*a* therefore has curved walls such that it extends partly around the sleeve 106, and forms a close fit with the outer surface of the sleeve and the inner surface of the tubular member. By forming the coolant conduit 108*a* in this flattened shape the maximum space for the flow of coolant is provided within the space between the bridging structures. By flattened, we mean that the coolant conduit has a cross sectional size D1 in the radial direction of the ablation probe that is less that the distance D2 it extends around the sleeve 116. In other embodiments, similarly shaped coolant conduits may be used to form the second coolant flow path in addition or alternatively to the conduit forming the first coolant flow path. In yet other embodiments, other shapes of coolant flow path may be used, such as those having a circular cross section.

Another embodiment of an ablation probe 200 is shown in FIGS. 12 to 16. The ablation probe 200 includes features corresponding to those of that shown in FIGS. 2 to 11, with corresponding reference numerals used for corresponding components. Any feature discussed in connection with the ablation probe of FIGS. 2 to 11 can be used in connection with the ablation probe of FIGS. 12 to 16, and vice versa.

In the embodiment shown in FIGS. 12 to 16, the bridging structures 214*a*, 214*b*, 214*c* of the ablation probe 200 are each formed from a tab connected at one end and extending outward from the body of the sleeve, rather than being connected at each end like the strips forming the bridging structures 114*a*, 114*b*, 114*c*. The tabs are bent at their point of connection with the body of the sleeve 216 such that they are splayed-out from the outer surface of the sleeve. They therefore also extend across the space between the feeding cable 204 and tubular member 206 which surrounds it. The tabs are similarly formed by cut-outs in the wall of the feed cable sleeve.

Figure 12:
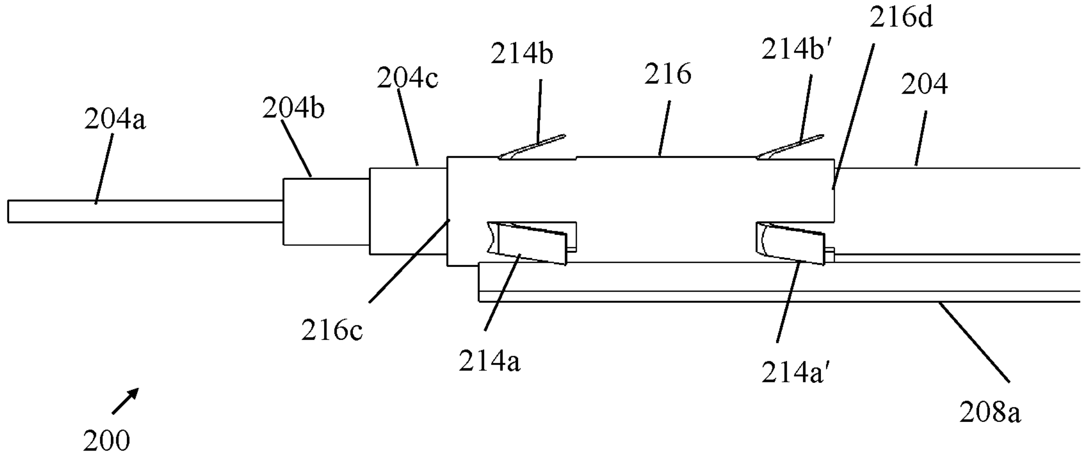
FIG. 12 shows a partly assembled side view of an ablation probe of another embodiment, without its tubular member and applicator assembly.

The bridging structures 214*a*, 214*b*, 214*c* may be located on the sleeve 216 similarly to those shown in FIGS. 2 to 11. As can be seen in FIG. 12, they may similarly comprise a first set of bridging structures 214*a*, 214*b*, 214*c* having an equal angular spacing around the longitudinal axis and spaced from the proximal end of the applicator by an odd multiple of a quarter wavelength as described above. In the presently described embodiment a second set of bridging structures 214*a*', 214*b*', 214*c*' is provided. The second set of bridging structures 214*a*', 214*b*', 214*c*' is located proximal to the first along the length of the ablation probe, and is spaced apart from the first by an odd multiple of a quarter wavelength as described above. Each of the sets of bridging structures in any embodiment described herein may comprise one or more axially aligned bridging structures.

In the described embodiment, the tabs do not extend past the distal 216*c* and proximal 216*d* edges of the sleeve, and so are in line with the body of the sleeve. They are therefore formed by cut-outs in the sleeve corresponding to the shape of the tabs. In other embodiments, the tabs may extend from the proximal and/or distal edges of the sleeve 216 (e.g. they may be cut-out from the edges so that they extend from the distal or proximal edges 216*c*, 216*d* of the sleeve 216 or other component from which they are formed).

The bridging structures 214*a*, 214*b*, 214*c*, 214*a*', 214*b*', 214*c* each extend an equal amount radially from the outer surface of the feed cable 204 (e.g. sleeve 216) and so provide concentric alignment between the feed cable 204 and tubular member 206. They also form a resiliently deformable structure similarly to those of the embodiment shown in FIGS. 2 to 11.

Figure 13:
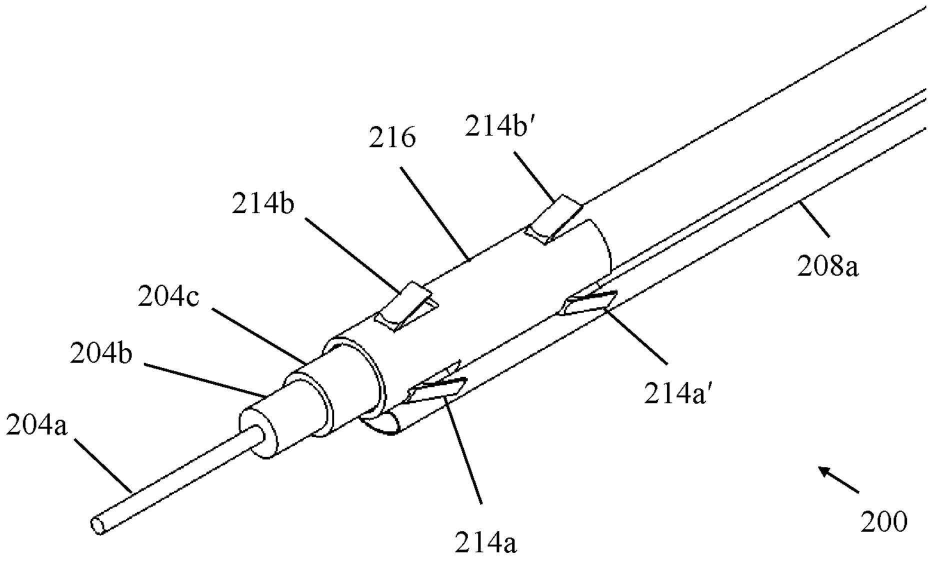
FIG. 13 shows a perspective view of the components shown in FIG. 12.
Figure 14:
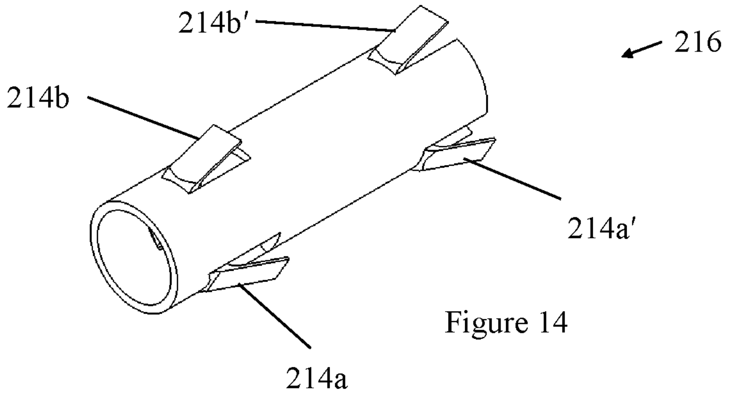
FIG. 14 shows a perspective view of a sleeve forming part of a choke of the ablation probe of FIG. 12.
Figure 15:
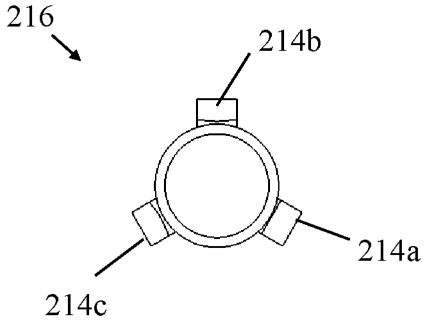
FIG. 15 shows a cross sectional view (in a plane normal to the longitudinal axis) of the sleeve shown in FIG. 14.

As can be seen in FIG. 13, the angular space between bridging structures 214*a*, 214*b*, 214*c*, 214*a*', 214*b*', 214*c* provides space for coolant flow paths to be provided along the length of the ablation probe similarly to as described above. The ranges of sizes described in connection with FIG. 10 and elsewhere herein apply equally to the bridging structures 214*a*, 214*b*, 214*c*, 214*a*', 214*b*', 214*c* formed from tabs rather than linking strips.

In previously described embodiments the bridging structures are provided on a sleeve forming part of the feed cable (e.g. forming a tight fit around the outer surface of the outer conductor of the feeding cable). In other embodiments, the bridging structures may be formed from other components while still bridging the space between the feeding cable and structure which houses it.

Figure 17:
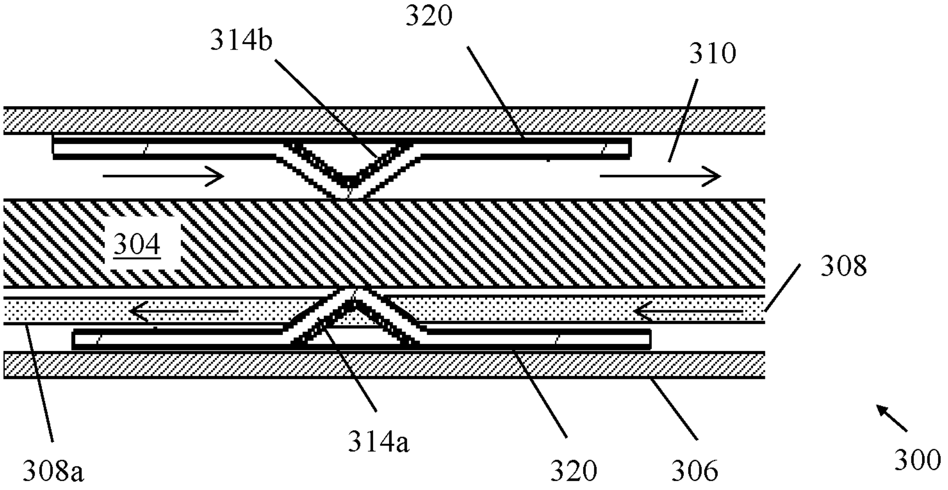
FIG. 17 shows a longitudinal cross sectional view of an ablation probe according to another embodiment showing an alternative arrangement of bridging structures forming a choke.

FIG. 17 illustrates a close up view of the bridging structures 314*a*, 114*b* of an ablation probe 300 according to another embodiment. FIG. 17 shows the region around the bridging structures, in which a feeding cable 304, tubular member 306, coolant conduit 308*a*, and second coolant flow path 310 are visible. In this embodiment, the tubular shaft 306 comprises a shaft sleeve 320 which is located within the tubular member 306. The shaft sleeve 320 replaces the feed cable sleeve 316 of the embodiments described elsewhere herein. The inner diameter of the tubular member 306 is approximately the same as the outer diameter of the shaft sleeve 320 to provide a close fitting contact between them. The bridging structures 314*a*, 314*b*, 314*c* are formed in the wall of the shaft sleeve 320, and extend radially towards the centreline of the ablation probe from the inside surface of the shaft sleeve 320. This allows them to bridge the space between the shaft and the feeding cable. The shaft sleeve 320 (and in some embodiments the tubular member) are formed from an electrically conductive material to form the choke.

Figure 18:
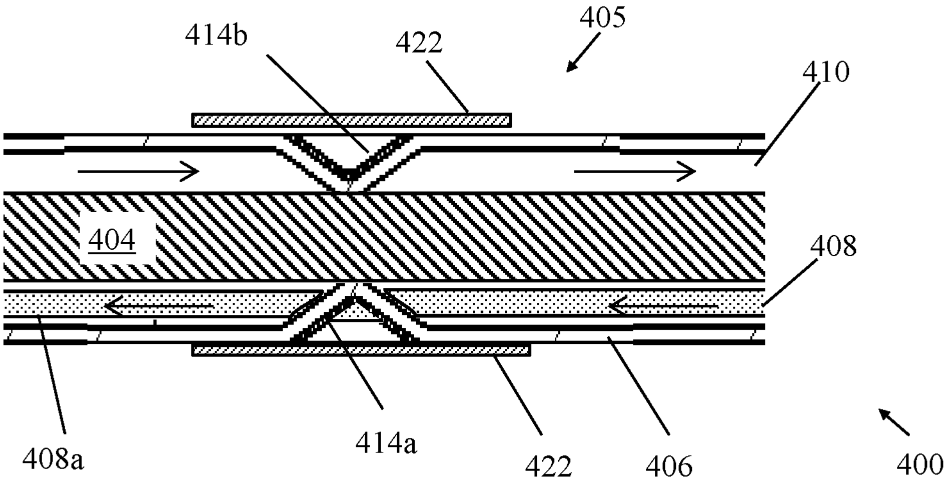
FIG. 18 shows a longitudinal cross sectional view of an ablation probe according to another embodiment showing a further alternative arrangement of bridging structures forming a choke.

FIG. 18 illustrates another alternative arrangement of the bridging structures. FIG. 18 shows a close up view of part of an ablation probe 400 around the bridging structures in which the feeding cable 404, tubular member 406, coolant conduit 408*a*, first and second coolant flow paths 408, 410 are visible. In this embodiment, the feed cable sleeve and shaft sleeve of other embodiments are absent, with the bridging structures being instead formed from the wall of the tubular member 406 that forms the tubular shaft 405. The tubular shaft 405 further comprises a sealing sleeve 422 extending around the outer surface of the tubular member 406 at the location of the bridging structures. The sealing sleeve is arranged to seal the cuts-outs in the wall of the tubular member 406 created to form the bridging structures. The sealing sleeve 422 may be a heat-shrink layer, or formed of a thin walled polyimide tube, or the like. In other embodiments, other seals may be provided to seal the coolant flow path within the tubular member 406. In this embodiment, the tubular member 406 forms part of the choke, and so is formed from an electrically conductive material, at least along the part of its length forming the coke.

Figure 16:
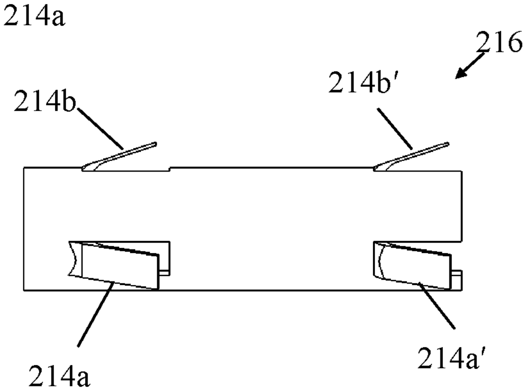
FIG. 16 shows a side view of the sleeve shown in FIG. 15.

In both of the embodiments shown in FIGS. 16 and 17 the bridging structures are formed from strips connected at each end to the sleeve or tubular member from which they are formed in the same way as those described in connection with FIGS. 2 to 11. In other embodiments, the bridging structures formed in the tubular member 406 or shaft sleeve 320 may be tabs similar to those described in connection with FIGS. 12 to 16.

In the previously described embodiments all of the bridging structures of each embodiment are of same type—e.g. all formed from connecting strips or all formed from tabs. This may aid manufacture. In other embodiments, different sets of bridging structures may be of different types, e.g. a first set of tabs and a second set of strips. In yet other embodiments, each of the bridging structures within a set may be different types.

The shapes of the bridging structures described above are examples only, with other shapes of angled or deformed region cut out from the relevant component being possible. In other embodiments, the bridging structures may not be straight sided tabs or strips as shown, but may have tapered or curved edges. In some embodiment, the bridging structures may not correspond to the size and shape of the cut-out left in the component from which they are formed (e.g. they may be further shaped once cut out).

Figure 19:
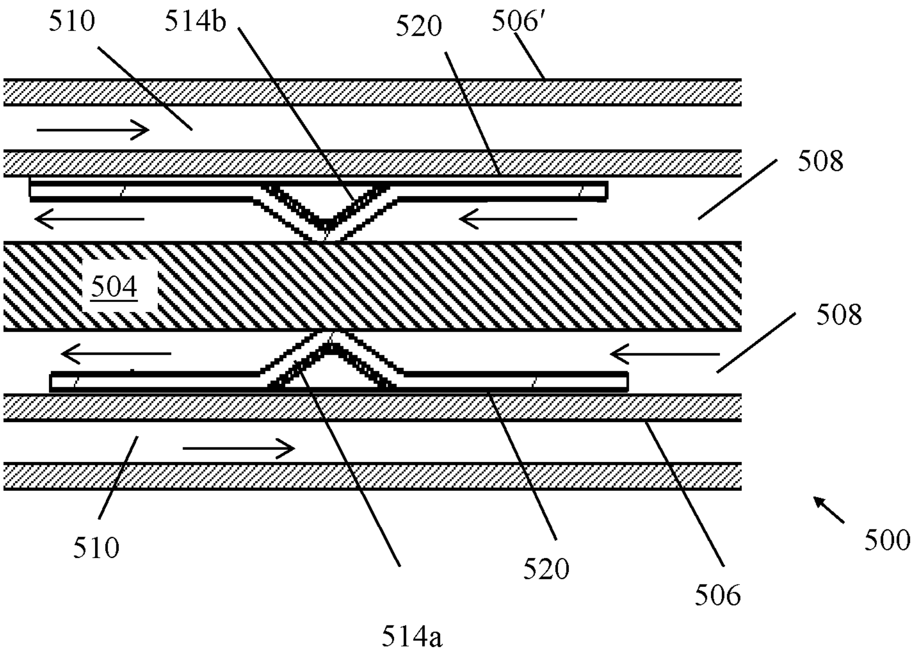
FIG. 19 shows a longitudinal cross sectional view of an ablation probe according to another embodiment showing an alternative arrangement of coolant flow paths.

In the embodiments already described both the first and second coolant flow paths are located within the tubular member e.g. between the tubular member 106, 206, 306, 406 and the feed cable 104, 204, 204, 304, 404. In other embodiments however, only one of the first and second coolant flow paths may be located within the tubular member. Such an embodiment is illustrated in FIG. 19, which shows an ablation probe 500 similar to that shown in FIG. 17. In the embodiment of FIG. 19, only the first coolant flow path 508 is located within the tubular member 506 and flows through the choke. The ablation probe 500 comprises a further second outer tubular member 506' extending around the first tubular member 506 of the previously described embodiments. An inside surface of the second tubular member 506' is spaced apart from outer surface of the first tubular member 506 to form the second coolant flow path 508 between them. Two concentric flow paths are therefore provided, each with a generally annular cross sectional shape (in a plane normal to the longitudinal axis). The flow of coolant is shown by the arrows in FIG. 19.

Any reference to an axial direction herein is defined as being parallel to the longitudinal axis labelled Y in FIG. 2. A radial direction is normal to the longitudinal axis Y. The length of the ablation probe is taken to be in a direction parallel to the longitudinal axis Y.

Various modifications will be apparent to the skilled person without departing form the scope of the claims. Any feature disclosed in connection with one embodiment may be used in combination with the features of another embodiment.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub-combination. The applicant hereby gives notice that new claims may be formulated to such features and/or combinations of such features during the prosecution of the present application or of any further application derived therefrom.

For the sake of completeness, it is also stated that the term "comprising" does not exclude other elements or steps, the term "a" or "an" does not exclude a plurality, a single processor or other unit may fulfil the functions of several means recited in the claims and any reference signs in the claims shall not be construed as limiting the scope of the claims.

The invention claimed is:

1. A microwave ablation probe, comprising:

an applicator arranged to apply microwave radiation to heat surrounding tissue;

a feed cable arranged to supply electromagnetic energy to the applicator;

a tubular shaft arranged to house at least part of the length of the feed cable;

a coolant flow path via which coolant is able to flow, the coolant flow path being located within a space between the tubular shaft and the feed cable; and a choke arranged to reduce power reflected from the applicator along the feed cable, wherein:

the choke comprises one or more bridging structures each provided on a component of the tubular shaft or the feed cable, the one or more bridging structures being arranged to extend across the space between the tubular shaft and the feed cable and form an electrical connection therebetween, the one or more bridging structures each extend only part way around a longitudinal axis of the ablation probe, thereby allowing coolant to flow through the choke, and the one or more bridging structures are each formed from an angled region cut out from a wall of the component of the tubular shaft or the feed cable from which they are formed.

2. A microwave ablation probe according to claim 1, wherein:

the feed cable comprises a feed cable sleeve forming an outer part of the feed cable electrically connected to an electrical conductor of the feed cable;

an outside surface of the feed cable sleeve is spaced apart from an inside surface of the tubular shaft to form the space in which the coolant flow path is located; and the one or more bridging structures are each formed from a region of the feed cable sleeve.

3. A microwave ablation probe according to claim 1, wherein:

the tubular shaft comprises a tubular member and a shaft sleeve located within the tubular member;

an outside surface of the feed cable is spaced apart from an inside surface of the shaft sleeve to form the space in which the coolant flow path is located; and the one or more bridging structures are each formed from a region of the shaft sleeve.

4. A microwave ablation probe according to claim 1, wherein:

the tubular shaft comprises a tubular member;

an outside surface of the feed cable is spaced apart from an inside surface of the tubular member to form the space in which the coolant flow path is located; and the one or more bridging structures are each formed from a region of the tubular member.

5. A microwave ablation probe according to claim 4, wherein the tubular shaft further comprises a sealing sleeve extending around the outer surface of the tubular member at the location of the bridging structures to seal cuts-outs in the wall of the tubular member formed by each of the one or more bridging structures.

6. A microwave ablation probe according to claim 1, wherein the angled region of each bridging structure extends out of alignment with an inner or outer surface of the component of the feed cable or tubular shaft from which it is formed.

7. A microwave ablation probe according to claim 1, wherein one or each of the one or more of the bridging structures comprises a bent strip extending between a distal section and a proximal section of the respective component of the tubular shaft or feed cable from which they are formed.

8. A microwave ablation probe according to claim 7, wherein each of the one or more bent strips have a rounded region at the point of contact with the other of the component of the tubular shaft or a component of the feed cable.

9. A microwave ablation probe according to claim 1, wherein one or each of the one or more bridging structures comprise a bent tab connected at one end to the body of the component of the feed cable or tubular shaft from which it is formed.

10. A microwave ablation probe according to claim 1, wherein each of the one or more bridging structures extend an angle around the longitudinal axis of the ablation probe in the range between 5° and 100°.

11. A microwave ablation probe according to claim 1, wherein the one or more bridging structures are arranged to concentrically align the feed cable and the tubular shaft.

12. A microwave ablation probe according to claim 1, wherein the one or more bridging structures is a plurality of bridging structures angularly spaced apart around a longitudinal axis of the ablation probe.

13. A microwave ablation probe according to claim 12, wherein the plurality of bridging structures are spaced apart by an angle around the longitudinal axis of the ablation probe in the range between 20° and 115°.

14. A microwave ablation probe according to claim 12, wherein the coolant flow path is a first coolant flow path, and the microwave ablation probe further comprises a second coolant flow path, the first coolant flow path being formed by a coolant conduit disposed within the tubular shaft, the coolant conduit extending along the longitudinal axis of the feed cable between two of the plurality of bridging structures.

15. A microwave ablation probe according to claim 14, wherein the coolant conduit is shaped to conform to the shape of an inner surface of the tubular shaft and an outer surface of the feed cable between which it extends.

16. A microwave ablation probe according to claim 14, wherein the coolant conduit has a flattened non-circular cross sectional profile in a plane normal to the longitudinal axis of the ablation probe.

17. A microwave ablation probe according to claim 12, wherein the one or more bridging structures comprises at least three spaced apart bridging structures.

* * * * *